US011096992B2

(12) United States Patent
Shi et al.

(10) Patent No.: US 11,096,992 B2
(45) Date of Patent: Aug. 24, 2021

(54) USE OF SEAPROSE TO REMOVE BACTERIAL BIOFILM

(71) Applicant: SMITH & NEPHEW, INC., Memphis, TN (US)

(72) Inventors: Lei Shi, Mansfield, TX (US); Aleksa Jovanovic, Fort Worth, TX (US); Catherine Van Der Kar, Grand Prairie, TX (US); Eric Roche, Fort Worth, TX (US)

(73) Assignee: SMITH & NEPHEW, INC., Memphis, TN (US)

( * ) Notice: Subject to any disclaimer, the term of this patent is extended or adjusted under 35 U.S.C. 154(b) by 0 days.

(21) Appl. No.: 14/399,124

(22) PCT Filed: May 10, 2013

(86) PCT No.: PCT/US2013/040514
§ 371 (c)(1),
(2) Date: Nov. 5, 2014

(87) PCT Pub. No.: WO2013/170128
PCT Pub. Date: Nov. 14, 2013

(65) Prior Publication Data
US 2015/0118219 A1    Apr. 30, 2015

Related U.S. Application Data

(60) Provisional application No. 61/645,815, filed on May 11, 2012, provisional application No. 61/820,915, filed on May 8, 2013.

(51) Int. Cl.

| | |
|---|---|
| *A61K 38/48* | (2006.01) |
| *A61L 26/00* | (2006.01) |
| *A61L 27/34* | (2006.01) |
| *A61L 29/08* | (2006.01) |
| *A61L 31/10* | (2006.01) |
| *A61L 27/54* | (2006.01) |
| *A61L 29/16* | (2006.01) |
| *A61L 31/16* | (2006.01) |
| *C12N 9/62* | (2006.01) |
| *A61K 45/06* | (2006.01) |
| *A61L 12/08* | (2006.01) |

(52) U.S. Cl.
CPC ............ *A61K 38/482* (2013.01); *A61K 45/06* (2013.01); *A61L 12/082* (2013.01); *A61L 26/008* (2013.01); *A61L 26/0014* (2013.01); *A61L 26/0066* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *C12N 9/62* (2013.01); *C12Y 304/21063* (2013.01); *A61L 2300/254* (2013.01); *A61L 2300/404* (2013.01)

(58) Field of Classification Search
CPC .. A61K 38/185; A61K 45/06; A61K 38/1808; C12N 15/8247; C12N 15/8282; C12N 9/0083; C12N 15/8218; C12N 9/0071; C12P 7/6427; C12P 7/6472
USPC ....................................................... 424/94.64
See application file for complete search history.

(56) References Cited

U.S. PATENT DOCUMENTS

| | | | |
|---|---|---|---|
| 4,197,291 A | 4/1980 | Klein et al. ................ | 424/94.65 |
| 5,902,600 A | 5/1999 | Woller et al. ................. | 424/445 |
| 6,172,219 B1 | 1/2001 | Callegaro et al. ......... | 536/123.1 |
| 6,399,092 B1 | 6/2002 | Hobson et al. ............... | 424/443 |
| 6,479,060 B1 | 11/2002 | Jones et al. .................. | 424/401 |
| 6,548,556 B2 | 4/2003 | Hobson et al. ............ | 514/772.4 |
| 7,294,497 B2 | 11/2007 | Kaplan ........................ | 435/200 |
| 7,459,155 B2 | 12/2008 | Margolin et al. .......... | 424/94.64 |
| 7,642,079 B2 | 1/2010 | Cayouette et al. ........... | 435/212 |
| 7,785,584 B2 | 8/2010 | Jones et al. ................ | 424/94.65 |
| 8,066,991 B2 * | 11/2011 | Jolly ................. | A61K 38/4873 |
| | | | 424/94.65 |
| 8,119,124 B2 | 2/2012 | Gorecki et al. ............. | 424/94.2 |
| 8,383,101 B2 * | 2/2013 | Olmstead ............ | A61K 9/0034 |
| | | | 424/94.2 |
| 8,632,769 B2 | 1/2014 | Barron ......................... | 424/94.1 |
| 8,809,031 B2 | 8/2014 | England et al. .............. | 435/202 |
| 9,694,100 B2 | 7/2017 | Shi et al. | |
| 10,058,596 B2 | 8/2018 | Hanson | |
| 2003/0026794 A1 * | 2/2003 | Fein ......................... | A61K 8/66 |
| | | | 424/94.2 |
| 2003/0027310 A1 | 2/2003 | Berka et al. .................. | 435/196 |
| 2003/0198631 A1 | 10/2003 | Shi et al. ................... | 424/94.63 |

(Continued)

FOREIGN PATENT DOCUMENTS

| | | |
|---|---|---|
| EP | 0590746 | 9/1993 |
| JP | 56092217 | 7/1981 |

(Continued)

OTHER PUBLICATIONS

Enzyme Handbook © Springer-Verlag Berlin Heidelber 1998 pp. 1-8.*

(Continued)

*Primary Examiner* — Louise W Humphrey
*Assistant Examiner* — Anjali Ajit Hirani
(74) *Attorney, Agent, or Firm* — Norton Rose Fulbright US LLP

(57) ABSTRACT

A method of disrupting a bacterial biofilm present on a surface, comprising applying a composition that includes a semi-alkaline protease produced by the fermentation of the fungus *Aspergillus melleus* (Seaprose) to the bacterial biofilm, wherein application of the composition to the bacterial biofilm disrupts the matrix of the bacterial biofilm.

12 Claims, 4 Drawing Sheets

(56) References Cited

U.S. PATENT DOCUMENTS

| | | | |
|---|---|---|---|
| 2003/0198632 A1 | 10/2003 | Shi et al. | 424/94.63 |
| 2005/0079594 A1 | 4/2005 | Marion | |
| 2005/0158299 A1* | 7/2005 | Margolin | A61K 38/482 |
| | | | 424/94.63 |
| 2007/0264715 A1 | 11/2007 | Robinson et al. | 435/471 |
| 2010/0124549 A1 | 5/2010 | Studin | 424/94.65 |
| 2010/0221237 A1 | 9/2010 | Kokai-Kun et al. | 424/94.67 |
| 2010/0254968 A1* | 10/2010 | Desser | A61K 38/4873 |
| | | | 424/94.64 |
| 2012/0258089 A1 | 10/2012 | Madhyastha et al. | 424/94.61 |
| 2013/0045196 A1 | 2/2013 | Shi et al. | |
| 2014/0154235 A1 | 6/2014 | Shi et al. | |
| 2015/0118219 A1 | 4/2015 | Shi et al. | |
| 2015/0283217 A1 | 10/2015 | Shi et al. | |
| 2016/0008293 A1 | 1/2016 | Shi et al. | |
| 2018/0289003 A1 | 10/2018 | Jovanovic et al. | |

FOREIGN PATENT DOCUMENTS

| | | | |
|---|---|---|---|
| JP | H06262165 | 9/1994 | |
| JP | 2008290966 | 12/2008 | |
| JP | 2010-126710 | 6/2010 | |
| WO | WO 02/051436 | 7/2002 | |
| WO | WO 2005/018695 | 3/2005 | |
| WO | WO 2005/047514 | 5/2005 | |
| WO | WO 2005/115357 | 12/2005 | |
| WO | WO 2006/037606 | 4/2006 | |
| WO | WO 2008/019417 | 2/2008 | |
| WO | WO 2009/068841 | 6/2009 | |
| WO | WO 2010079209 A2 * | 7/2010 | A61L 15/18 |
| WO | WO2010/112848 | 10/2010 | |
| WO | WO2011/063394 | 5/2011 | |
| WO | WO 2011/071986 | 6/2011 | |
| WO | WO2012/155027 | 11/2012 | |
| WO | WO 2014145037 A1 * | 9/2014 | A61K 31/683 |

OTHER PUBLICATIONS

James, G.A. et al.: "Biofilms in Chronic Wounds", Wound Repair Regen, vol. 16, (2008), pp. 37-44.

Kiedrowski, M.R. et al.: "New approaches for treating *Staphylococcal* biofilm infections", Ann. N.Y. Acad. Sci., vol. 1241, (2011), pp. 104-121.

Morihara, K. et al.: "Comparative study of various serine alkaline proteinases from microorganisms. Esterase activity against N-acylated peptide ester substrates", Archives of Biochemistry and Biophysics, vol. 165, (1974), pp. 72-79.

Nakatani, H, et al.: "Interaction of Asp. melleus Semi-alkaline protease with benzeneboronic acid", J. Biochem., vol. 81(5), (1972), pp. 1269-1272.

Spadari, S. et al.: "Highly restricted specificity of the serine proteinase aspergillopeptidase B", Biochimica et Biophysica Acta, vol. 359, (1974), pp. 267-272.

Turková, J. et al.:, "Alkaline proteinases of the genus *Aspergillus*", Biochimica et Biophysica Acta, vol. 257, (1972), pp. 257-263.

Akiyama et al., "Recent Investigations of *Staphylococcus aureus* in Dermatology", Japanese journal of Dermatology, 109(13), 1999, pp. 2095-2102. (English Abstract).

Notice of Reasons for Rejection (Translation) dated Mar. 15, 2017, issued in corresponding Japanese application No. 2015-511734.

Ogawa et al., "The Evaluation of the Effect of Bromelain Ointment on the Debridement of Eschar of Burn, Decubitus and Various Wound", Journal of New Remedies & Clinics, 48(10), 1999, pp. 1301-1309. (English Abstract).

Shi et al., "Evaluation Of Wound Debridement Efficacy Of Proteolytic Enzymes From The Fungus Aspergillus Melleus", Wound Repair and Regeneration, 20(2), 2012, pp. A39. (Abstract Only).

Barbera et al., "Multicentre clinical study on seaprose S in acute and chronic respiratory inflammation", *Minerva Cardioangiol*, 35(4):49-156, 1996.

Bracale and Selvetella, "Clinical study of the efficacy of and tolerance to seaprose S in inflammatory venous disease. Controlled study versus serration-peptidase", *Minerva Cardioangiol*, 44(10):515-524, 1996.

Braga et al., "Effects of Seaprose on the Rheology of Bronchial Mucus in Patients with Chronic Bronchitis. A Double-Blind Study vs. Placebo", *Int. J. Clin. Pharm. Res.*, 8(3):179-185, 1993.

Braga et al., "In Vitro Rheological Assessment of Mucolytic Activity Induced by Seaprose", *Pharmacological Research*, 22(5):611-617, 1990.

Dindelli et al., "Clinical efficacy and safety of Seaprose S in the treatment of surgical wound complications in puerperium", *Minerva Cardioangiol*, 42(7-8):313-315, 1990.

Drug Information Sheet; Teoase Tablets, 15mg, Revised Mar. 2008, 1 page.

Fossati, "Antiinflammatory Effects of Seaprose-S on Various Inflammation Models", *Drugs Exptl. Clin. Res.*, 25(6):263-270, 1999.

International Preliminary Report on Patentability issued in PCT Application No. PCT/US2012/037480, dated Nov. 21, 2013.

International Search Report and Written Opinion issued in PCT Application No. PCT/US2012/037480, dated Jul. 16, 2012.

Luisetti et al., "Some Properties of the Alkaline Proteinase From Aspergillus Melleus", *Int. J. Tiss. Reac.*, 13(4):187-192, 1991.

Miyazaki et al., "The Effect of SA-001 (Jeoase) on the Pharyngolaryngeal Complications Following Endotracheal Anesthesia", *Masui (Anesthesia)*, 18(8):722-730, 1969.

Moretti et al., "Effects of Seaprose on Sputum Biochemical Components in Chronic Bronchitic Patients: A Double-Blind Study vs. Placebo", *Int. J. Clin. Phar. Res*, 8(5):275-280, 1993.

Sasaki, Database WPI, Tomson Scientific, XP-002678257, Dec. 4, 2008.

"Research on Microbial Biofilms" National Institutes of Health, PA No. PA-03-047, 2002, Accessed from the Internet on Jan. 15, 2019, URL < https://grants.nih.gov/grants/guide/pa-files/pa-03-047.html >.

Ahn et al., "Robust trypsin coating on electrospun polymer nanofibers in rigorous conditions and its uses for protein digestion" *Biotechnol. Bioeng.*, 2010, 107:917-923.

Bjarnsholt "Why chronic wounds will not heal: a novel hypothesis" *Wound Repair and Regeneration*, 2008, 16(1):2-10.

Borriello et al., "Oxygen Limitation Contributes to Antibiotic Tolerance of *Pseudomonas aeruginosa* in Biofilms" *Antimicrobial Agents and Chemotherapy*, 2004, 48(7):2659-2664.

International Search Report and Written Opinion issued in International Patent Application No. PCT/IB2017/054535, dated Oct. 27, 2017.

Jacobsen "Investigating the humoral immune response in chronic venous leg ulcer patients colonised with *Pseudomonas aeruginosa*" *International Wound Journal*, 2011, 8(1):33-43.

Mertz, "Cutaneous Biofilms: Firend or Foe?" *Wounds*, 2003, 15:1-9.

Page, "Description of Skin Lesions" Merck Manual, 2016, Accessed from the Internet on Jan. 15, 2019, URL < https://www.merckmanuals.com/professional/dermatologic-disorders/approach-to-the-dermatologic-patient/description-of-skin-lesions >.

Polini et al., "Collagen-functionalised electrospun polymer fibers for bioengineering applications" *Soft Matter*, 2010, 6:1668-1674.

Sugimoto et al., "*Staphylococcus epidermidis* Esp Degrades Specific Proteins Associated with *Staphylococcus aureus* Biofilm Formation and Host-Pathogen Interaction" *Journal of Bacteriology*, 2013, 195(8):1645-1655.

Van der Kar et al., "A Versatile In Vitro biofilm Model Using Two Wound Pathogens to Screen Formulations" *2010 Wound Healing Society Annual Meeting*, Poster BRC09, 2010.

Williamson et al., "Heterogeneity in *Pseudomonas aeruginosa* Biofilms Includes expression of Ribosome Hibernation Factors in the Antibiotic-Tolerant Subpopulation and Hypoxia-Induced Stress Response in the Metabolically Active Population" *Journal of Bacteriology*, 2012, 194(8):2062-207.

Zheng et al., "Penetration of Rifampin through *Staphylococcus epidermidis* Biofilms" *Antimicrobial Agents and Chemotherapy*, 2002, 46(3):900-903.

Office Action issued in corresponding Japanese application No. 2019-050562, dated Mar. 2, 2020.

(56) References Cited

OTHER PUBLICATIONS

Phillips et al., "Bacterial biofilms in wounds" *Wound Healing Southern Africa* 2008, 1(2), 10-12.
Schierle et al., "*Staphylococcal* biofilms impair wound healing by delaying reepithelialization in a murine cutaneous wound model" *Wound Repair and Regeneration* 2009, 17(3), 354-359.
Attinger et al., "Clinically Addressing Biofilm in Chronic Wounds" *Advances in Wound Care* 2012, 1(3), pp. 127-132.
O'Meara et al., "Antibiotics and antiseptics for venous leg ulcers" *Cochrane Database of Systematic Reviews* 2014, Issue 1, Abstract only, pp. 1-4.
Braga et al., "The influence of seaprose on erythromycin penetration into bronchial mucux in bronchopulmonary infections," *Drugs Exp. Clin. Res.* 1992; 18(3): 105-111.
Office Action issued in Chinese Application No. 2013800367052, dated Aug. 29, 2017.
Falanga, Vincent. "Wound Bed Preparation and the Role of Enzymes: A Case for Multiple Actions of Therapeutic Agents," *Wounds*, 2002; 14(2): 47-50.
Notice for Reasons for Rejection issued in Japanese Application No. 2015-511734, dated Jul. 6, 2017 (English translation provided).
Ohjimi , "Wounds and Infection—Clinical Conditions and Diagnosis of Wound Infections and Therapeutic Strategies Therefore," *Plastic and Reconstructive Surgery Today*, 2010; 6: 1-5.
Tiwari, V., "Burn Wound: How it Differs from Other Wounds?" *Indian Journal of Plastic Surgery*, 2012; 45(2): 364-373.

\* cited by examiner

USE OF SEAPROSE TO REMOVE BACTERIAL BIOFILM

CROSS REFERENCE TO RELATED APPLICATIONS

This application is a national phase application under 35 U.S.C. § 371 of International Patent Application No. PCT/US2013/040514 filed May 10, 2013, which claims the benefit of U.S. Provisional Application Ser. No. 61/820,915, filed May 8, 2013, and the benefit of U.S. Provisional Application Ser. No. 61/645,815, filed May 11, 2012. The contents of the referenced applications are incorporated into the present application by reference.

BACKGROUND OF THE INVENTION

A. Field of the Invention

The present invention generally relates to methods and compositions useful for treating biofilms. The compositions can include Seaprose as an active ingredient.

B. Description of Related Art

Biofilms are populations of bacteria or fungi attached to an inert or living surface. Bacteria in a biofilm are enmeshed in an extracellular polymer matrix, generally a polysaccharide matrix, which holds the bacteria together in a mass, and firmly attaches the bacterial mass to the underlying surface. Evidence has shown that biofilms constitute a significant threat to human health. The Public Health Service estimates that biofilms are responsible for more than 80% of bacterial infections in humans (National Institutes of Health, 1998 RFA #DE-98-006). Biofilms are involved in health conditions such as urinary tract infections, cystitis, lung infections, skin infections, sinus infections, ear infections, acne, dental caries, periodontitis, nosocomial infections, open wounds, and chronic wounds. Bacteria growing in biofilms exhibit increased resistance to antibiotics and antimicrobials and are very difficult to eliminate.

Wounds and skin lesions are especially susceptible to bacterial infection. From a microbiological perspective, the primary function of normal, intact skin is to control microbial populations that live on the skin surface and to prevent underlying tissue from becoming colonized and invaded by potential pathogens. Exposure of subcutaneous tissue such as a wound or skin lesion provides a moist, warm and nutritious environment that is conducive to microbial colonization and proliferation. Since bacterial colonization in a wound is mostly polymicrobial, involving numerous microorganisms that are potentially pathogenic, any wound or skin lesion is at high risk of becoming infected.

Wounds often have multiple barriers to healing. Wound healing and infection is influenced by the relationship between the ability of bacteria to create a stable, prosperous community within a wound environment and the ability of the host to control the bacterial community. Since bacteria are rapidly able to form their own protective microenvironment following their attachment to a surface, i.e., a biofilm, the ability of the host to control these organisms is likely to decrease as the biofilm community matures, ultimately affecting the ability of the wound to heal. Wounds in which healing is delayed, i.e., chronic wounds, are of particular concern with respect to biofilm formation. Some have linked biofilms to chronic wounds (Mertz, 2003, Wounds, 15: 1-9). Wounds such as diabetic foot ulcers, venous leg ulcers, arterial leg ulcers, decubitus ulcers, stasis ulcers, burns, and pressure ulcers are examples of wounds which may become chronic wounds. Bacterial biofilms in chronic wounds are generally not resolved by the host's immune system, and these biofilms have an increased resistance to systemic and topical antimicrobial/antibiotic agents. Accordingly, bacterial biofilm infections in chronic wounds are very difficult to eliminate.

Particularly virulent organisms in wounds are gram-positive bacteria such as *staphylococcus* spp., *streptococcus* spp., and *enterococci* spp. Biofilms of *Staphylococcus aureus*, including resistant strains such as methicillin resistant *Staphylococcus aureus* (MRSA), have become increasingly problematic in wounds and skin lesions. These organisms, especially MRSA, can reside in the anterior nares and cause skin lesions in the nose which can also spread to other parts of the body, causing skin lesions at those sites.

In recent years, there have been numerous efforts to use various antibiotics and antimicrobials for the treatment of non-healing, clinically infected skin lesions and chronic wounds. These antimicrobial agents are of varying chemical compounds and include, among others, peptides such as vancomycin, antimicrobials such as mupirocin, and silver/silver ions. However, certain gram-positive bacteria, such as *Staphylococcus aureus*, including MRSA, have become increasingly resistant to these compounds.

SUMMARY OF THE INVENTION

The inventors have discovered that Seaprose can be used to disrupt and remove biofilms from surfaces.

In one instance, there is disclosed method of disrupting a bacterial biofilm present on a surface, comprising applying a composition that includes Seaprose to the bacterial biofilm, wherein application of the composition to the bacterial biofilm disrupts the matrix of the bacterial biofilm. The surface can be on an animate or inanimate object. For example, the surface can be skin or a wound. The wound can be a chronic wound (non-limiting examples include a diabetic foot ulcer, a venous leg ulcer, an arterial leg ulcer, a decubitus ulcer, a stasis ulcer, a dermal ulcer, a burn, or a pressure ulcer). In some instances, the wound can include necrotic tissue (such as, for example, eschar). The compositions of the present invention can debride the necrotic tissue. In one aspect, the surface can be an epithelial surface (non-limiting examples include a portion of an oral cavity, a portion of a corneal surface, a portion of a reproductive tract, a portion of a urinary tract, a portion of a respiratory tract, a portion of a gastrointestinal tract, a portion of a peritoneum, a portion of a middle ear, or a portion of a prostate). A non-limiting example of a surface of an inanimate object can be a medical implant device (such as, for example, a catheter, a stent, a bone plate, screw, pin, or rod, a spinal disc, an ear tube, or a contact lens). In certain aspects, the composition can include 0.0001 to 1% or 0.001 to 1% by weight of Seaprose (amounts and ranges below and above these ranges are also contemplated—e.g., amounts of 0.000001, 0.0001, 1.5%, 2%, 3%, 4%, 5%, 6%, 7%, 8%, 9% 10%, or more). The Seaprose can be isolated or purified. The composition can be formulated for topical or injectable application. Examples of such formulations can be gels, creams, ointments, pastes, and solutions. In one particular instance, the composition can further include glycerin polyacrylate clatharate, glycerin, an emulsifying wax, or petrolatum, or any combination thereof. In certain aspects, the composition does not include hydroxyethylcellulose. The bacterial biofilm can be a gram-negative bacterial biofilm. A non-limiting example of a gram-negative biofilm includes a biofilm produced by *Pseudomonas* bacteria. A non-limiting example of a *Pseudomonas* bacteria is *Pseudomonas aerugi-* nosa. In other aspects, the bacterial biofilm can be a gram-positive bacterial biofilm. A non-limiting example of a gram-positive bacterial biofilm is one produced by a Staphylococcal bacteria. A non-limiting example of a Staphylococcal bacteria is *Staphylococcus aureus*. The *Staphylococcus aureus* bacterial can be methicillin-resistant Staphylococcal *aureus* (MRSA). Also contemplated is removal of at least a portion of the biOfilm from a surface after said biofilm has been disrupted with a composition of the present invention. The composition can further include an anti-microbial agent (examples include an antibiotic agent, an anti-fungal agent, an antiseptic, or a cleaning agent—the specification also provides examples of these agents below). In some instances, the method further comprises application of a second composition to the bacterial biofilm before, during, or after the Seaprose containing composition is applied to the bacterial biofilm. The second composition can include an anti-microbial agent (such as those mentioned above).

Also contemplated is a composition for disrupting a bacterial biofilm comprising an effective amount of Seaprose and an acceptable carrier. As explained above, the composition can include 0.0001 to 1% or 0.001 to 1% by weight of Seaprose (amounts and ranges below and above these ranges are also contemplated—e.g., amounts of 0.000001, 0.0001, 1.5%, 2%, 3%, 4%, 5%, 6%, 7%, 8%, 9% 10%, or more). The Seaprose can be isolated or purified Seaprose. The acceptable carrier can be a pharmaceutically acceptable topical carrier or a pharmaceutically acceptable injectable carrier. The composition can be formulated as a gel, cream, solution, paste, or ointment. In a particular instance, the composition can be an ointment comprising petrolatum, a gel comprising glycerin polyacrylate clathrate, or a cream comprising glycerin and an emulsifying wax. In certain aspects, the composition does not include hydroxyethylcellulose. The bacterial biofilm can be a gram-negative bacterial biofilm. A non-limiting example of a gram-negative biofilm includes a biofilm produced by *Pseudomonas* bacteria. A non-limiting example of a *Pseudomonas* bacteria is *Pseudomonas aeruginosa*. In other aspects, the bacterial biofilm can be a gram-positive bacterial biofilm. A non-limiting example of a gram-positive bacterial biofilm is one produced by a Staphylococcal bacteria. A non-limiting example of a Staphylococcal bacteria is *Staphylococcus aureus*. The *Staphylococcus aureus* bacterial can be methicillin-resistant *Staphylococcus aureus* (MRSA). The composition can further include an anti-microbial agent (examples include an antibiotic agent, an anti-fungal agent, an antiseptic, or a cleaning agent—the specification also provides examples of these agents below). The anti-microbial agent can be effective against a specific bacteria (such as, for example, a Staphylococcal bacteria (e.g., *Staphylococcus aureus*) or a *Pseudomonas* bacteria (e.g., *Pseudomonas aeruginosa*)).

Also contemplated are kits that include any one of the compositions disclosed throughout the specification and claims. In certain embodiments, the composition is comprised in a container. The container can be a bottle, dispenser, or package. The container can dispense a predetermined amount of the composition. In certain aspects, the composition is dispensed in a spray, dollop, or liquid.

It is contemplated that any embodiment discussed in this specification can be implemented with respect to any method or composition of the invention, and vice versa. Furthermore, compositions of the invention can be used to achieve methods of the invention.

The terms "inhibiting," "reducing," "treating," or any variation of these terms means any measurable decrease or complete inhibition or removal of a biofilm from a surface. The term "disrupting," or any variation of this term, means any measurable decrease or breakdown of at least a portion of the matrix of a bacterial biofilm. Further, the compositions of the present invention can also be used to prevent the formation of a biofilm on a surface through application of said compositions to a surface that may be susceptible of developing a bacterial biofilm.

The phrase "bacterial biofilm" means a biofilm that has been formed by a bacteria (e.g., gram-positive or gram-negative bacteria).

The phrase "gram-positive bacterial biofilm" means a bacterial biofilm that has been formed by gram-positive bacteria.

The phrase "gram-negative bacterial biofilm" means a bacterial biofilm that has been formed by gram-negative bacteria.

The term "effective," as that term is used in the specification and/or claims, means adequate to accomplish a desired, expected, or intended result.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the composition's ability to disrupt a bacterial biofilm.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Figure 1:
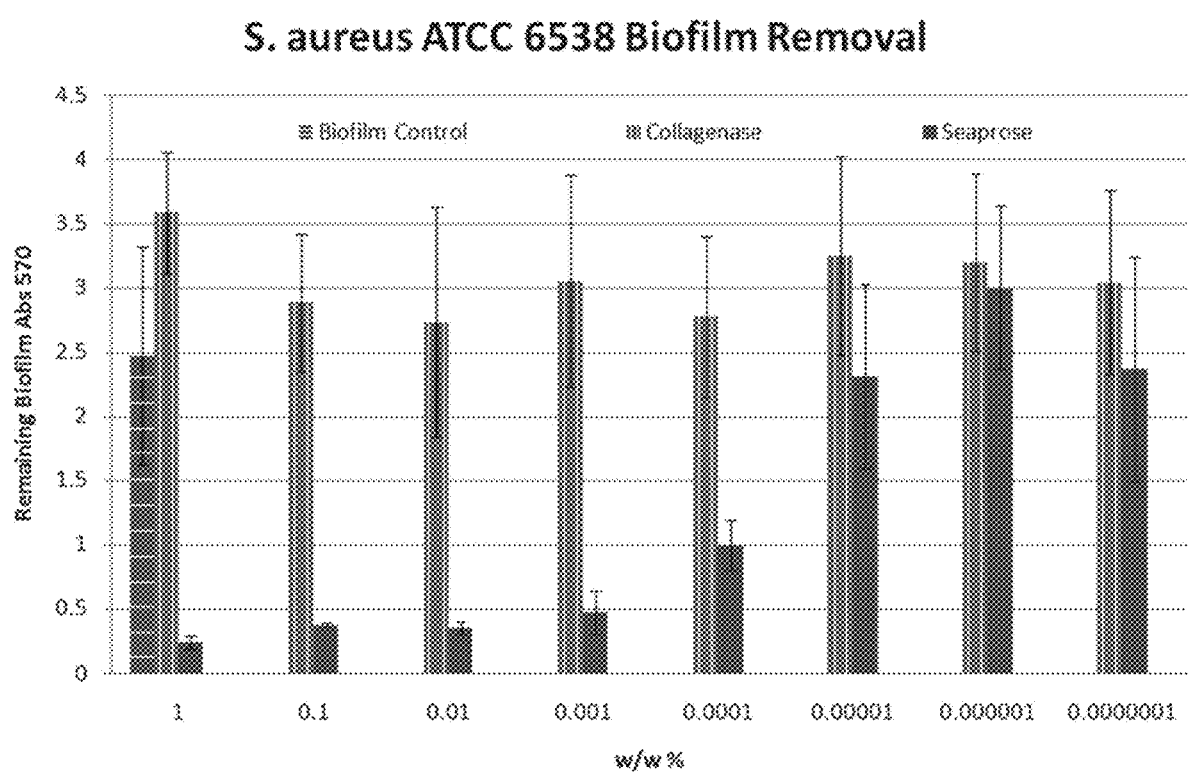
FIG. 1. A graph showing the effectiveness of Seaprose in removing a *S. aureus* bacterial biofilm when compared with collagenase and a control.

Bacterial biofilms are present in several health conditions that afflict the population. Examples of such conditions include urinary tract infections, cystitis, lung infections, skin infections, sinus infections, ear infections, acne, dental caries, periodontitis, nosocomial infections, open wounds, and chronic wounds.

One of the unique aspects of the present invention is the inventors' discovery that Seaprose can be used to disrupt or remove bacterial biofilms from a surface that has a bacterial biofilm. An example of such a surface is a skin wound. These and other non-limiting aspects of the present invention are described in further detail in the following subsections.

A. Compositions

The compositions of the present invention can be used to combat the presence of bacterial biofilms. Such compositions include an effective amount of Seaprose to achieve this result. The compositions can also include a pharmaceutically acceptable carrier (e.g., topical carrier or injectable carrier). The compositions of the invention may further comprise pharmaceutically active ingredients, cosmetically active ingredients, and vulnerary agents (e.g., growth factors) suitable for topical or injectable administration to wounds.

1. Seaprose

Seaprose is a semi-alkaline protease produced by the fermentation of the fungus *Aspergillus melleus* and is commercially available in a powder form from Amano Enzyme, Inc., Japan under the trade name SEAPROSE S®. Seaprose may be prepared by either a liquid or solid fermentation process using techniques known by one of skill in the art. Seaprose has also been referred to as onoprose, promelase, promelasum, Jeoase, FLAMINASE® (Prodotti Formenti S.r.l., Milan Italy), and *Aspergillus melleus* semi-alkaline proteinase.

The major protease in Seaprose is a semi-alkaline protease with a molecular weight around 31 kDa. It can also contain other enzymes such as amylase, which is a hydrolytic enzyme which breaks down carbohydrates. Alternatively, Seaprose can be purified or isolated by standard techniques known to those of skill in the art. Seaprose shows great stability at an optimal pH range of 5 to 9, and an optimal temperature below 50° C. These conditions are suitably for application of the enzyme in wounds and favorable for drug formulation and manufacture.

Seaprose has previously been used for a variety of medical indications and treatment; however, it has never previously been used in a topical or injectable form for use as an anti-biofilm agent. For example, Seaprose has been shown to possess in-vitro mucolytic activity (Braga 1990) and to effectively treat patients with bronchitis by oral administration of Seaprose capsules (Braga 1993), (Moretti 1993). Seaprose has shown anti-inflammatory activity against many different inflammatory conditions in animal models (Fossati 1991). Seaprose was shown to be effective in treating patients with inflammatory venous disease by oral administration of Seaprose tablets (Bracale 1996). Seaprose has been used to treat abdominal pain due to pancreatitis (U.S. Pat. No. 7,459,155). Seaprose has been used to treat complications of puerperal surgical wounds by oral administration of Seaprose 30 mg tablets (Dindelli 1990).

According to the present invention, Seaprose may be in a dissolved state and/or a dispersed state in the pharmaceutically acceptable carrier. The Seaprose may also be encapsulated. It may also be used neat without a carrier. Seaprose can also be used in a purified or isolated form.

The amount of Seaprose in a composition with a pharmaceutically acceptable carrier is an amount effective for wound debridement and can generally range from about 0.001% w/w to about 10% w/w; or from about 0.01% to about 9%; or from about 0.1% to about 8%; or from about 0.1% to about 0.9%; or from about 0.2% to about 0.8%; or from about 0.3% to about 0.7%; or from about 0.4% to about 0.6%; or about 0.5%; or from about 0.5% to about 7%; or about 1% to about 6%; or from about 1.5% to about 5%; or from about 0.5% to about 1.5%; or from about 0.6% to about 1.4%; or from about 0.7% to about 1.3%; or from about 0.8% to about 1.2%; or from about 0.9% to about 1.1%; or about 1%. Such amount will be that amount which effectively debrides necrotic tissue in wounds. In particular embodiments, a range of 0.0001 to 1% or 0.001 to 1% can be used.

2. Pharmaceutically Acceptable Carriers

The compositions of the present invention may comprise various pharmaceutically acceptable carriers suitable for topical delivery and compatible with Seaprose. Non-limiting examples include lotions, creams, emulsions, ointments, gels, pastes, solutions, aerosol sprays, aerosol foams, non-aerosol sprays, non-aerosol foams, powders, liquid solutions, liquid suspensions, films, and sheets. The compositions may be impregnated in gauzes, bandages, or other wound dressing materials for topical delivery.

The compositions of the invention may further comprise functional ingredients suitable for use in topical compositions and compatible with Seaprose. Non-limiting examples include absorbents, antimicrobial agents, antioxidants, binders, buffering agents (including Tris buffer solutions), bulking agents, chelating agents, colorants, biocides, deodorant agents, emulsion stabilizers, film formers, fragrance ingredients, humectants, lytic agents, enzymatic agents, opacifying agents, oxidizing agents, pH adjusters, plasticizers, preservatives, reducing agents, emollient skin conditioning agents, humectant skin conditioning agents, moisturizers, surfactants, emulsifying agents, cleansing agents, foaming agents, hydrotopes, solvents, suspending agents, viscosity control agents (rheology modifiers), viscosity increasing agents (thickeners), and propellants. Listings and monographs of the functional ingredients described herein are disclosed in The International Cosmetic Ingredient Dictionary and Handbook (INCI), 12$^{th}$ Edition, 2008, hereby incorporated by reference.

Non-limiting examples of antimicrobial agents include anti-fungal agents such as Miconazole Nitrate, Econazole Nitrate, and others, and antibiotics such as Neomycin, Bacitracin, Polymixin, etc. Additional non-limiting antimicrobial agents that can be used include Benzalkonium Chloride, Benzethonium Chloride, Benzoic Acid or salt form thereof, Benzoyl Peroxide, Benzyl Alcohol, Bispyrithione Salt, Borage Oil, Boric Acid, Cadexomer-Iodine, Camphorated Metacresol, Camphorated Phenol, Chlorhexidine Gluconate, Chlorobutanol, Cloflucarban, Dapsone, Dehydroacetic Acid or salt form thereof, Ethyl Alcohol, Eucalyptol, Extracts of Lavender Oil, Free fatty acids having from six to eighteen carbons, Glyceryl Laurate, Hexachlorophene, Hexitidine, Hexylresorcinol, Hydrogen Peroxide, Hydroxybenzoic Acids or salt forms thereof, Iodine Complexed with Phosphate Ester of Alkylaryloxy Polyethylene, Iodine Tincture, Iodine Topical Solution, Iodoquinol, Isopropyl Alcohol, Lipacide CG, Mafenide Acetate, Magnesium Pyrithione, Menthol, Merbromin, Mercufenol Chloride, Methyl Salicylate, Methylbenzethonium Chloride, Methylparaben, Metronidazole, Metronidazole derivatives, Nitrofurazone, Nonyl Phenoxypoly Ethanol-Iodine, n-Propanol, Organic Peroxides, p-chloro-m-xylenol, Phenol, Phenoxyethanol, Phenyl Alcohol, Poloxamer-iodine complex, Povidone Iodine, PVP-Iodine, Rose Hips Oil, Salicylic Acid, Secondary Amyltricresols, Selenium sulfide, Silver or salt form thereof, Silver Sulfadiazine, Sodium Oxychlorosene, Sodium Sulfacetmide, Sorbic Acid or salt form thereof, Sulfur, Tetrachlorosalicylanilide, Thymol, Tribromsalan, Triclocarbon, Triclosan, Undecoylium Chloride-iodine Complex, Zinc Pyrithione. In addition, antimicrobial peptides and proteins can be used.

Suitable pharmaceutically acceptable topical carriers include an anhydrous hydrophilic wound debrider composition as disclosed in: U.S. Pat. No. 6,548,556 herein incorporated by reference; a spray-on topical wound debrider composition as disclosed in U.S. Pat. No. 7,785,584 herein incorporated by reference; an enzymatic wound debriding composition as disclosed in international PCT application PCT/US10/59409 herein incorporated by reference; a hydrogenated castor oil ointment as disclosed in U.S. Pat. No. 6,479,060 herein incorporated by reference; an anhydrous hydrophilic absorbent wound dressing as disclosed in U.S. Pat. No. 6,399,092 herein incorporated by reference; and a hydrogel wound dressing as disclosed in U.S. Pat. No. 5,902,600 herein incorporated by reference.

The compositions of the present invention may also comprise various pharmaceutically acceptable carriers suitable for injectable delivery compatible with Seaprose.

The compositions of the present invention may be packaged in any package configuration suitable for topical or injectable products. Non-limiting examples for topical products include bottles, lotion pumps, toddles, tubes, jars, non-aerosol pump sprayers, aerosol containers, syringes, pouches, and packets. The packages may be configured for single-use (one dose) or multiple-use administration. Non-limiting examples for injectable products include vials, syringes, micro-needle syringes, or bags.

The compositions of the present invention may also be sterile. They may be sterilized via an aseptic manufacturing process or sterilized after packaging by methods known in the art.

3. Manufacture

The compositions of the present invention may be manufactured by suitable processing methods known by one of skill in the art for topical and/or injectable products. For example, Seaprose can be admixed with the pharmaceutically acceptable carrier. Further, the compositions can be sprayed onto a surface. Alternatively, Seaprose can be applied to a bacterial biofilm in a neat form (e.g., without carrier).

B. Methods of Use

The composition of the present invention may be used in methods for treating, disrupting, or removing bacterial biofilms from a surface or with preventing or limiting the formation of a bacterial biofilm on a surface that is susceptible of developing a bacterial biofilm (such as, for example, a wound, a surgical incision or wound, an implanted device, etc.). Such methods can include applying (e.g., topical, injectable, sprayable etc.) to a bacterial biofilm or target surface a composition comprising Seaprose. After application, the bacterial biofilm can be covered with a dressing such as a gauze pad. Alternatively, or additionally, the surface can then be treated with a traditional anti-microbial agent to attack the bacteria remaining within the bacterial biofilm. The composition can also or alternatively be applied to a dressing such as a gauze pad first and then applied to a bacterial biofilm. The application amount can depend on the type and severity of the bacterial biofilm. Further, application of the composition can be in the form of a regimen with period application (e.g., hourly, daily, weekly, etc.). As explained above, a wide range of surfaces that have bacterial biofilms can be treated with the compositions of the present invention. For instance, wound surfaces present on a person's skin can be treated. Such wound surfaces can be, by way of example, burns, acute wounds, or chronic wounds that include a bacterial biofilm or are susceptible to formation of a bacterial biofilm. Other types of surfaces that could have bacterial biofilms (e.g., living tissue, bodily surfaces, inanimate objects) or are susceptible in developing bacterial biofilms (e.g., wounds, surgical incision or wounds, medical implant devices, etc.) can be treated with the compositions of the present invention.

EXAMPLES

The following examples are included to demonstrate certain non-limiting aspects of the invention. It should be appreciated by those of skill in the art that the techniques disclosed in the examples which follow represent techniques discovered by the applicants to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Exemplary Formulations

The following Tables provide non-limiting examples of formulations containing Seaprose of the present invention:

TABLE 1

Gel*

| Ingredient | % Concentration (by weight) |
| --- | --- |
| SEAPROSE S | 1.0 |
| Tris Buffer Solution (TBS) 10 mM (pH 7.5) | 96.4 |
| Hydroxyethylcellulose (HEC) | 2.6 |
| TOTAL | 100 |

*Procedure: A gel was made with the HEC and Tris buffer. SEAPROSE S was admixed with the HEC gel. The viscosity of the gel gradually reduced over time possibly due to the amylase present in the Seaprose material degrading the HEC.

TABLE 2

Gel*

| Ingredient | % Concentration (by weight) |
| --- | --- |
| SEAPROSE S | 1.0 |
| CURASOL ® Gel Wound Dressing | 99.0 |
| TOTAL | 100 |

*Procedure: SEAPROSE S was admixed with the CURASOL Gel Wound Dressing to form a clear gel. The viscosity was maintained over time.

TABLE 3

Cream*

| Ingredient | % Concentration (by weight) |
|---|---|
| SEAPROSE S | 0.5 |
| Tris Buffer Solution (TBS) 10 mM (pH 7.5) | 71.52 |
| Glycerin | 7.0 |
| Methylparaben | 0.2 |
| Propylparaben | 0.08 |
| Emulsifying Wax | 15.2 |
| Isopropyl Palmitate NF | 5.5 |
| TOTAL | 100 |

*Procedure: Methylparaben, propylparaben and glycerin were dissolved in the Tris buffer solution at 70° C. Emulsifying wax and isopropyl palmitate were added to the above solution at 70° C. and mixed to form an emulsion, The emulsion was cooled to 35° C. at which time SEAPROSE S was admixed with the emulsion. A white cream was obtained.

TABLE 4

Ointment*

| Ingredient | % Concentration (by weight) |
|---|---|
| SEAPROSE S | 0.5 |
| White Petrolatum | 78.5 |
| PEG-600 | 20.0 |
| Poloxamer-407 | 1.0 |
| TOTAL | 100 |

*Procedure: An Active Phase was made by melting a mixture of half of the amount of PEG-600 and half of the amount of poloxamer-407 at 70° C., cooling the mixture to 35° C. at which time SEAPROSE S was admixed with the mixture. A Main Phase was made by melting a mixture of white petrolatum and the remaining half of the amount of PEG-600, and the remaining half of the amount of poloxamer-407 at 70° C., cooling the mixture to 35° C. after the homogenization and melting of poloxamer-407. The Active Phase was then admixed with the Main Phase. The resulting mixture was mixed at RT for 45 minutes.

TABLE 5

Capmul Oil Based Formulation*

| Ingredient | % Concentration (by weight) |
|---|---|
| SEAPROSE S | 0.5 |
| Capmul MCM, NF | 20 |
| Tris Buffer Solution (TBS) 10 mM (pH 7.5) | q.s. |
| Poloxamer-407 | 12.75 |
| TOTAL | 100 |

*Procedure: Poloxamer-407 was solubilized at 4° C. in TBS buffer (10 mM TBS), upon solubilization, the oil, Capmul MCM NF, from Abitec, was added and the mixture was mixed at RT under high shear until homogeneous. Seaprose S was solubilized at calculated concentration in TBS, upon solubilization, the solution was added to the cream and mixed for 30 min at RT. Off-white cream was obtained.

Example 2

In Vitro Biofilm Removal Data

An in vitro assay was performed to demonstrate the bacterial biofilm disruption and removal capabilities of Seaprose. In this assay, S. aureus ATCC 6538 was suspended in tryptic soy broth supplemented with 0.25% glucose for optimal bacterial biofilm formation. The suspension was transferred to the wells of sterile 96 well plates and incubated for 22 hours at 37° C. with one change of media. After bacterial biofilm formation the media was replaced with enzyme treatments prepared in growth media. After 16 hours of treatment (treatment composition included Seaprose S+above mentioned growth medium) the remaining attached bacteria were quantified by aspirating media and washing the plate thoroughly followed by crystal violet staining and recording the absorbance at 570 nm. The crystal violet stains the remaining attached bacteria and a decreased absorbance compared to control indicates removal of attached bacteria. FIG. 1 provides a summary of these data. As illustrated in FIG. 1, Seaprose was far more effective at disrupting and removing the bacterial biofilm than collagenase at levels ranging from 1% w/w to 0.0000001% w/w, with a surprising level of efficacy at levels of 1% w/w to 0.0001% w/w, and even more surprising levels of 1% w/w to 0.001% w/w. The surprising nature of this discovery is based on the general knowledge that proteases are not thought to be overly effective on their own in disrupting or removing bacterial biofilms.

Figure 2:
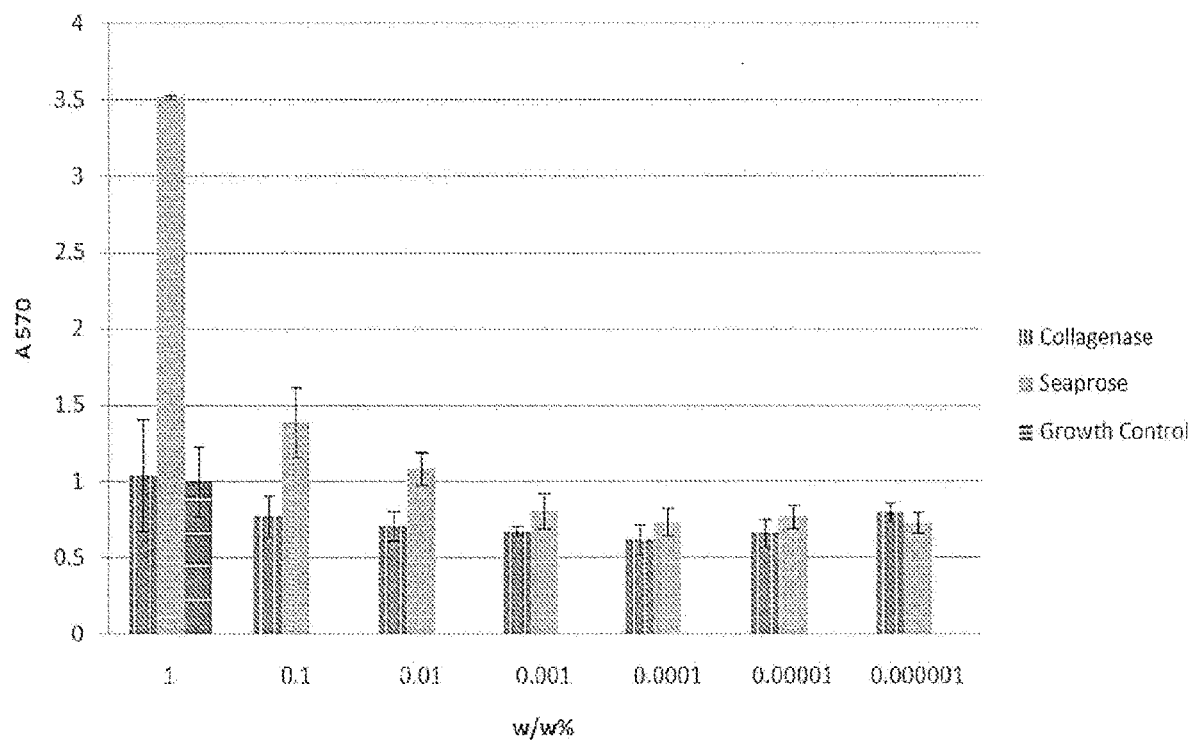
FIG. 2. A graph showing the effectiveness of Seaprose in removing a *P. aeruginosa* bacterial biofilm when compared with collagenase and a control.

An in vitro assay was also performed to demonstrate the bacterial biofilm disruption and removal capabilities of Seaprose on P. aeruginosa. In this assay, P. aeruginosa ATCC 15442 was suspended in phosphate buffered saline with 10% Tryptic soy broth and 0.45% glucose. The suspension was transferred (200 microliters) to the wells of sterile 96 well plates and incubated for 26 hours at 37° C. with one change of media. After biofilm formation, the media was replaced with enzyme treatments previously prepared in growth media. After 18 hours of treatment at 37° C. (treatment composition included Seaprose S+above mentioned growth medium) the remaining attached bacteria were quantified by aspirating the media and washing the plate thoroughly followed by crystal violet staining and recording the absorbance at 570 nm. The crystal violet stains the remaining attached bacteria and a decreased absorbance compared to the growth control indicates removal of attached bacteria. FIG. 2 provides a summary of these data.

Example 3

In Vivo Biofilm Removal Data

An in vivo assay was performed to demonstrate the bacterial biofilm disruption and removal capabilities of Seaprose on methicillin-resistant S. aureus (MRSA) containing biofilms. The assay was similar to that described in E. D. Roche, P. J. Renick, S. P. Tetens, and D. L. Carson, 2012, A Model for Evaluating Topical Antimicrobial Efficacy against Methicillin-Resistant Staphylococcus aureus Biofilms in Superficial Murine Wounds, Antimicrobial Agents and Chemotherapy, 56, 4508-10.

In particular, twenty-eight female, SKH1 mice were administered Cytoxan injections four days prior to the wounding. Overnight cultures were prepared of the MRSA 33592, which were streaked to confirm purity. Prior to wounding, the inoculum was prepared and adjusted to $2.0 \times 10^9$ cfu/mL (colony forming unit/milliliter). The inoculum was spot plated to confirm the challenge cfu and placed on ice for the duration of the wound creation and inoculation procedures. All wounding, treatment applications, and dressing changes were conducted with the animals under anesthesia, administered via isoflurane inhalant. The surgical field was sterilized with povidone-iodine followed by an alcohol swab. The skin was blotted dry with sterile gauze before wounding. Using a pre-cut template, the wounds were created using a rotary tool, on a low speed, by repeatedly touching the skin for 5 seconds at a time. The wounds were wiped with saline moistened gauze to clear the wound of any debris created by the rotary tool prior to inoculation. Each wound was inoculated with 10 μL of inoculum and dressed with a pre-moistened spot band-aid.

Secondary dressings of a layer of Surgilast® size 1 dressing secured at the distal end with a strip of Elastikon® were applied after dressing the inoculated wounds. Each mouse was placed in a heated recovery tub until conscious and moving before being returned to the animal room.

The mice were organized in seven groups, with four mice in each group. Each treatment was present in two treatment groups, opposite a different treatment in each case. Initial treatments, at timepoint 0, were applied 24 hours after inoculation. A second treatment was applied at 24 hours. The wounds were photographed at wounding, each treatment application, and study end. Three mice from each group were sampled for microbiology 48 hours after the initial treatment was applied. The microbiology samples were obtained with 4 mm biopsy punches and placed in pre-labeled, pre-weighed tubes containing PBS (phosphate buffered saline) solution. The samples were placed on ice until further processing could take place. Once all the samples were obtained, the samples were allowed to warm to room temperature for re-weighing. Once re-weighed, the samples were homogenized at 30,000 rpm for 10 second intervals until the sample was completely disrupted. Once fully homogenized, the sample was placed back on ice until all samples were processed. The samples were used to create dilution plates, with duplicates of all samples, for spot plating on TSA and Charcoal agars. The spot plates were grown overnight in a 37° incubator before the colonies were counted. The colony counts were converted into log cfu/g and graphed. Data is presented in FIGS. 3 and 4, which confirms Seaprose had an effect in reducing MRSA bioburden in a mouse MRSA wound biofilm model beyond the oil base in which it was present. The oil base+Seaprose (referenced as "Seaprose (in Base)" in FIGS. 3 and 4) also trended toward a greater effect than a silver gel (SilvaSorb® Gel obtained from Medline Industries, Inc., Mundelein, Ill. (USA).

Figure 3:
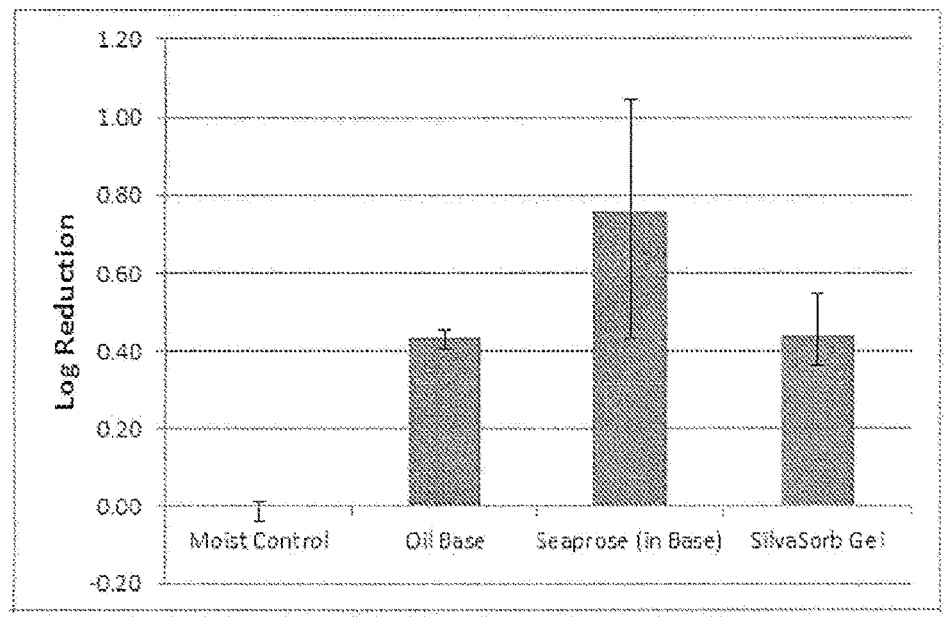
FIG. 3. A graph showing the effectiveness of Seaprose in removing a methicillin-resistant *S. aureus* (MRSA) biofilm in a mouse model.
Figure 4:
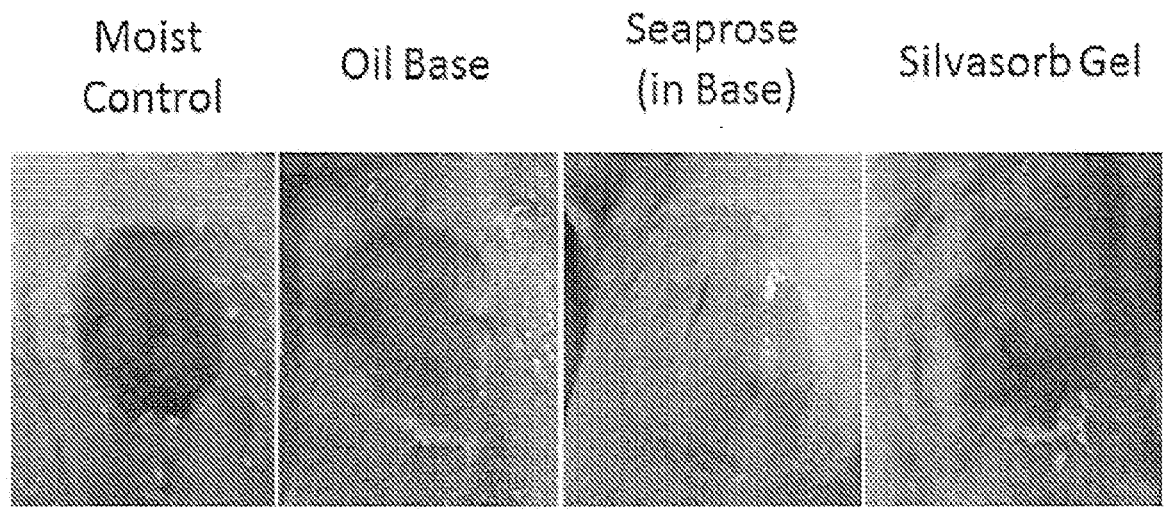
FIG. 4. Photos of wounds after treatment with Seaprose and comparators (pretreated wounds had dense MRSA biofilm in a mouse model).

The oil base and oil base-Seaprose formulas referenced above and noted in FIGS. 3 and 4 are provided in Tables 6 and 7, respectively.

TABLE 6

Oil Base*

| Ingredient | % Concentration (by weight) |
| --- | --- |
| Poloxamer-407 | 13.513 |
| Capmul MCM NF | 20.033 |
| Tris Buffer Solution (TBS) 10 mM (pH 7.5) | 66.454 |
| TOTAL | 100 |

*Procedure: Poloxamer-407 was solubilized at 4° C. in TBS buffer (10 mM TBS), upon solubilization, the oil, Capmul MCM NF, from Abitec, was added and the mixture was mixed at RT under high shear until homogeneous. Off-white cream was obtained.

TABLE 7

Oil Base + Seaprose S

| Ingredient | % Concentration (by weight) |
| --- | --- |
| Poloxamer-407 | 12.761 |
| Capmul MCM NF | 19.974 |

TABLE 7-continued

Oil Base + Seaprose S

| Ingredient | % Concentration (by weight) |
| --- | --- |
| SEAPROSE S | 0.501 |
| Tris Buffer Solution (TBS) 10 mM (pH 7.5) | 66.764 |
| TOTAL | 100 |

*Procedure: Poloxamer-407 was solubilized at 4° C. in TBS buffer (10 mM TBS), upon solubilization, the oil, Capmul MCM NF, from Abitec, was added and the mixture was mixed at RT under high shear until homogeneous. Seaprose S was solubilized at calculated concentration in TBS, upon solubilization, the solution was added to the cream and mixed for 30 min at RT. Off-white cream was obtained.

Example 4

In Vitro Digestion of Pig Burn Eschar

The gel formula in Table 1 (1% Seaprose Gel) and each of the following two gel formulas (1% Thermolysin Gel (Table 8) and 10% Bromelain Gel (Table 9)) were used in an in-vitro study to compare the degradation of pig eschar by each gel formula.

TABLE 8

1% Thermolysin Gel

| Ingredient | % Concentration (by weight) |
| --- | --- |
| Thermolysin (Sigma-Aldrich) | 1.0 |
| Tris Buffer Solution 10 mM (pH 7.5) | 95.1 |
| Hydroxyethylcellulose (HEC) | 2.9 |
| Sodium Chloride | 0.9 |
| Calcium Chloride | 0.1 |
| TOTAL | 100 |

TABLE 9

10% Bromelain Gel

| Ingredient | % Concentration (by weight) |
| --- | --- |
| Bromelain (Spectrum) | 10.0 |
| Water | 84.6 |
| Carbomer 980K | 1.9 |
| Disodium Phosphate | 2.6 |
| 4-Chloro-3-Methylphenol | 0.1 |
| Sodium Hydroxide | 0.8 |
| TOTAL | 100 |

The study was conducted in-vitro using eschar materials obtained from pig burn wounds. The eschar materials were dried completely. The dry weight was used as baseline. Samples of the dried eschar weighing 40-60 mg were moisturized with 50 µl of Tris buffered saline. The moisturized eschar samples were immersed in 3 g of each of the three gel formulas. The gels with eschar were stored at 37° C. for 24 hours. After 24 hours, the samples were centrifuged at 5000 rpm for 5 minutes. The supernatant was discarded and water was added to wash the precipitates. The samples were centrifuged again. Another wash step was performed and then the precipitates were freeze-dried. The dry weights of the precipitates were used to calculate the degradation percentage based on the baseline dry weights. The results are presented in FIG. 5.

Figure 5:
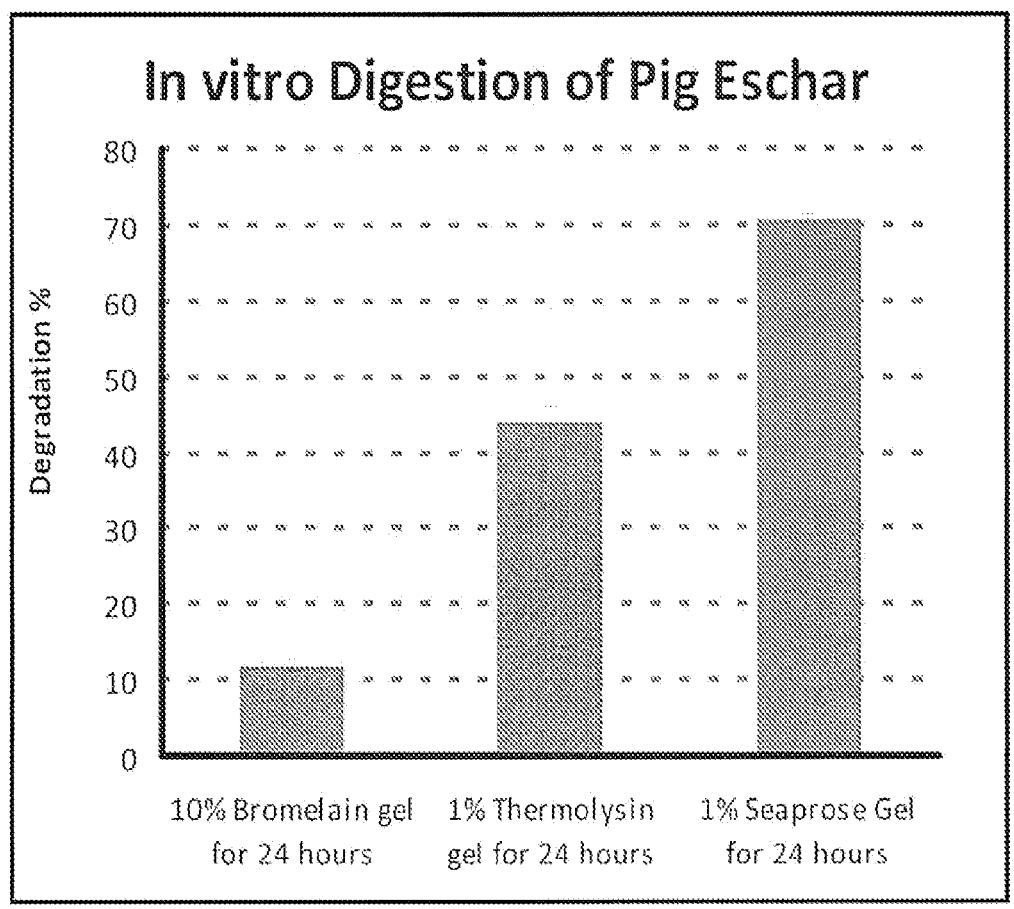
FIG. 5. A plot of the results of an in-vitro study comparing the degradation of pig eschar by bromelain, thermolysin, and Seaprose gels at 37° C. within a 24-hour period.

The results in FIG. 5 demonstrate that the Seaprose gel was more effective and exhibited superior potency in digesting the eschar material as compared to the 1% thermolysin gel (Table 8) and 10% bromelain gel (Table 9) within the 24 hour period. The quickness at which the Seaprose gel digested the eschar as compared to the 1% thermolysin gel and the 10% bromelain gel was unexpected, because thermolysin and bromelain are both known in the art to be a fast debriding enzymes (see, e.g., U.S. Patent Publication 2003/0198631 and U.S. Pat. No. 8,119,124, respectively). The results of the in-vitro study indicate that Seaprose can efficiently and effectively target and digest eschar proteins and therefore, it is suitable as a superior enzymatic wound debrider which can be used for the treatment of wounds in need of debridement.

Example 5

In Vivo Debridement of Pig Burn

Figure 6:
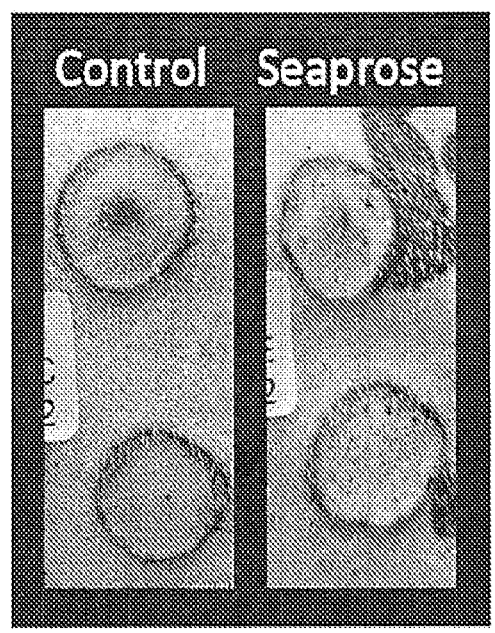
FIG. 6. An image of in vivo pig wounds after 24 hour treatment with a Seaprose hydrogel compared with a control (moist wound care).
Figure 7:
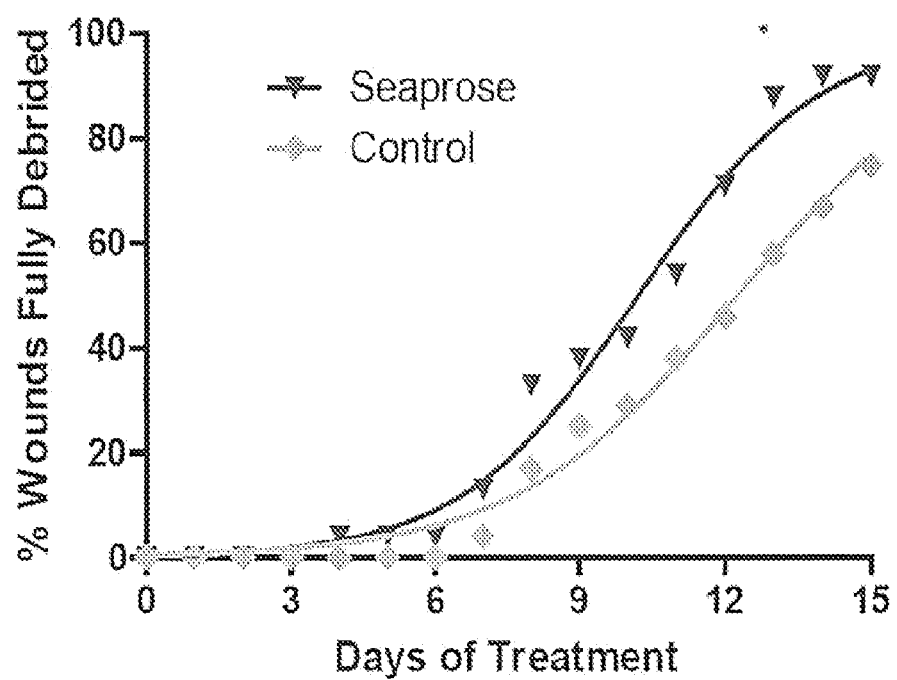
FIG. 7. A graph of the results of the in-vivo pig study comparing the debridement of wounds with Seaprose hydrogel compared with a control (moist wound care).

In this in vivo pig study, eschars were formed on the backs of pigs by introducing burn wounds using heated brass rods and allowing the formation of dry eschars over several days. There was a visual effect of Seaprose (SAP) on many wounds in comparison to control after one day of treatment (FIG. 6). Overall, SAP exhibited more rapid complete debridement of the eschars when compared against a control (non-adherent pre-moistened wound dressing with saline) (FIG. 7).

The particulars of this in vivo study are as follows. Pigs were anesthetized, the torso shaved with clippers and a razor, and washed with vedadine. Then an isopropyl rinse was performed to sterilize the surgical field. Twenty 2-cm wounds were created on the dorsum of each pig. The wounds were created using solid brass rods, heated to 100° C. in sand baths, held on the skin for 45 seconds. The wounds were left to dry for five days, giving the eschars time to form, with protective foam dressings being replaced every other day during eschar formation. After eschar formation and on a daily basis for treatments, the wounds were cleaned, photographed, treated according to the treatment randomization scheme, and dressed with non-adherent dressings (pre-moistened with saline) secured with Transpore tape and occlusive secondary dressings. Statistical significance for the number of eschars fully debrided was determined using Fisher's Exact test.

Treatment regimen for this study included use of a Seaprose containing formulation prepared in the following manner and a control which consisted of a non-adherent pre-moistened wound dressing with saline): (1) Seaprose S powder was prepared (see Table 10 below) and 100 mg of said powder was directly applied to the wound; and (2) a gel was prepared (see Table 11 below) and 400 mg of said gel was applied on top of the Seaprose S powder. Treatments were performed once a day for a fifteen day period. After the initial 24 hours of treatment, visual differences were apparent for many Seaprose-treated wounds, including pitting of the eschar and in some cases limited exposure of healthy wound tissue (FIG. 6). Over the fifteen day treatment period, Seaprose treatment produced a consistent trend of complete debridement of more wounds than the control (Seaprose treatment achieved statistical significance ($p<0.05$) versus the control on day 13 of treatment) (FIG. 7).

TABLE 10

Seaprose S Powder*

| Ingredient | % Concentration (by weight) |
| --- | --- |
| SEAPROSE S | 2.0 |
| Sorbitol | 98.0 |
| TOTAL | 100 |

*Process: Seaprose S and sorbitol were mixed at room temperature (approximately 20 to 25° C.) to obtain a homogenous powder.

TABLE 11

Gel*

| Ingredient | % Concentration (by weight) |
| --- | --- |
| Hispagel-200 | 31.86 |
| Tris Buffer Solution 10 mM (pH 7.5) | 58.37 |
| Imidurea | 0.14 |
| Glycerin | 9.45 |
| Methylparaben | 0.16 |
| Propylparaben | 0.02 |
| TOTAL | 100 |

*Process: Preservatives were mixed in Tris Buffer at high temperature (>70° C.) along with glycerin. Upon cooling, Hispagel-200 was added. Clear and transparent gel was obtained.

REFERENCES

Publications

Turková, J., Mikes, O., Hayashi, K., Danno, G. and Polgár, L. Alkaline proteinases of the genus *Aspergillus*. *Biochim. Biophys. Acta* 257 (1972) 257-263.

Morihara, K., Oka, T. and Tsuzuki, H. Comparative study of various serine alkaline proteinases from microorganisms. Esterase activity against N-acylated peptide ester substrates. *Arch. Biochem. Biophys.* 165 (1974) 72-79.

Spadari, S., Subramanian, A. R. and Kalnitsky, G. Highly restricted specificity of the serine proteinase aspergillopeptidase B. *Biochim. Biophys. Acta* 359 (1974) 267-272.

Nakatani H, Fujiwake H, Hiromi K., Interaction of *Asp. melleus* Semi-alkaline protease with benzeneboronic acid. *J Biochem* 1977 May; 81(5):1269-72.

James, G. A., Swogger, E., Wolcott, R., Pulcini, E. dL., Secor, P., Sestrich, J., Costerton, J. W., Stewart, P. S. Biofilms in Chronic Wounds. *Wound Rep. Reg.* 2008, 16, 37-44.

Kiedrowski, M. R. and Horswill, A. R., New approaches for treating staphylococcal biofilm infections. *Ann. N.Y. Acad. Sci.* 2011, 1241, 104-121.

The invention claimed is:

1. A method of disrupting a bacterial biofilm present on a wound that does not include necrotic tissue, the method consisting of applying a composition consisting of seaprose and a pharmaceutically acceptable carrier to the bacterial biofilm present on the wound, wherein seaprose is a semi-alkaline protease produced by the fermentation of the fungus *Aspergillus melleus*, wherein application of the composition to the bacterial biofilm disrupts the matrix of the bacterial biofilm, wherein the semi-alkaline protease has a molecular weight of about 31 kDa, wherein the pharmaceutically acceptable carrier is selected from a lotion, cream, emulsion, ointment, gel, paste, solution, aerosol spray, aerosol foam, non-aerosol spray, non-aerosol foam, powder, liquid solution, liquid suspension, film, and sheet, and wherein seaprose is the only enzymatic agent in the composition.

2. The method of claim 1, wherein the wound is a chronic wound.

3. The method of claim 2, wherein the chronic wound is a diabetic foot ulcer, a venous leg ulcer, an arterial leg ulcer, a decubitus ulcer, a stasis ulcer, a dermal ulcer, a burn, or a pressure ulcer.

4. The method of claim 1, wherein the composition includes 0.0001 to 1% by weight of seaprose.

5. The method of claim 1, wherein the seaprose is isolated or purified seaprose.

6. The method of claim 1, wherein the pharmaceutically acceptable carrier is a gel, cream, ointment, solution, or paste.

7. The method of claim 1, wherein the composition is topically applied to the wound.

8. The method of claim 1, wherein the bacterial biofilm is a gram-positive bacterial biofilm.

9. The method of claim 8, wherein the bacterial biofilm includes Staphylococcal bacteria.

10. The method of claim 9, wherein the bacteria is *Staphylococcus aureus*.

11. The method of claim 10, wherein the bacteria is methicillin-resistant *Staphylococcus aureus* (MRSA).

12. The method of claim 1, wherein applying the composition removes a portion of the bacterial biofilm from the wound.

\* \* \* \* \*